(12) United States Patent
Ye et al.

(10) Patent No.: US 9,983,109 B2
(45) Date of Patent: May 29, 2018

(54) YIELD STRESS MEASUREMENT DEVICE AND RELATED METHODS

(71) Applicant: Halliburton Energy Services, Inc., Houston, TX (US)

(72) Inventors: Xiangnan Ye, Cypress, TX (US); Dale E. Jamison, Humble, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 391 days.

(21) Appl. No.: 14/890,876

(22) PCT Filed: Dec. 15, 2014

(86) PCT No.: PCT/US2014/070361
§ 371 (c)(1),
(2) Date: Nov. 12, 2015

(87) PCT Pub. No.: WO2016/099442
PCT Pub. Date: Jun. 23, 2016

(65) Prior Publication Data
US 2016/0356689 A1 Dec. 8, 2016

(51) Int. Cl.
*G01N 11/04* (2006.01)
*E21B 7/00* (2006.01)
(Continued)

(52) U.S. Cl.
CPC ............... *G01N 11/04* (2013.01); *E21B 7/00* (2013.01); *E21B 49/08* (2013.01); *G01N 2011/0033* (2013.01)

(58) Field of Classification Search
CPC ............ G01N 11/04; E21B 7/00; E21B 49/08
See application file for complete search history.

(56) References Cited

U.S. PATENT DOCUMENTS 2,279,121 A * 4/1942 Kistler .................... G04F 1/066
200/33 A
2,799,646 A * 7/1957 Lacey ...................... C09K 8/28
507/134
(Continued)

FOREIGN PATENT DOCUMENTS

WO         03008936 A2    1/2003
WO      2016099442 A1    6/2016

OTHER PUBLICATIONS

International Search Report and Written Opinion for PCT/US2014/070361 dated Sep. 30, 2015.
(Continued)

*Primary Examiner* — John Fitzgerald
(74) *Attorney, Agent, or Firm* — McDermott Will & Emery LLP

(57) ABSTRACT

A yield stress measurement device and corresponding methods may use a two-capillary tube setup that measures the amount of a fluid drawn into each capillary and correlates that to the yield stress of the fluid. The devices and corresponding methods may be particularly useful for in-the-field measurements at well sites during drilling operations or other wellbore operations. An exemplary yield stress measurement apparatus may include a first capillary tube and a second capillary tube substantially perpendicular to each other, each capillary tube having two open ends and a length extending therebetween; a first and second length scale coupled to the lengths of the first and second capillary tubes, respectively; and a first fluid area and a second fluid area at one of the open ends of each of the first and second capillary tubes, respectively.

19 Claims, 5 Drawing Sheets

(51) Int. Cl.
*E21B 49/08* (2006.01)
*G01N 11/00* (2006.01)

(56) References Cited

U.S. PATENT DOCUMENTS

| | | | | |
|---|---|---|---|---|
| 6,412,336 B2 * | 7/2002 | Shin | ............... | A61B 5/02035 600/573 |
| 6,450,974 B1 | 9/2002 | Kim et al. | | |
| 6,484,565 B2 * | 11/2002 | Shin | ............... | A61B 5/02035 73/54.01 |
| 6,484,566 B1 * | 11/2002 | Shin | ............... | A61B 5/02035 324/71.1 |
| 6,523,396 B2 * | 2/2003 | Shin | ............... | A61B 5/02035 73/54.04 |
| 6,564,618 B2 * | 5/2003 | Shin | ............... | A61B 5/02035 324/71.1 |
| 6,571,608 B2 * | 6/2003 | Shin | ............... | A61B 5/02035 73/54.01 |
| 6,598,465 B2 * | 7/2003 | Shin | ............... | A61B 5/02035 324/71.1 |
| 6,732,573 B2 * | 5/2004 | Shin | ............... | A61B 5/02035 424/78.38 |
| 6,745,615 B2 * | 6/2004 | Kensey | ............... | A61B 5/02035 73/54.01 |
| 6,796,168 B1 * | 9/2004 | Goldstein | ............... | A61B 5/02035 324/71.1 |
| 6,907,772 B2 | 6/2005 | Kensey et al. | | |
| 7,581,435 B2 * | 9/2009 | Pelletier | ............... | G01N 11/04 73/54.02 |
| 2001/0039828 A1 | 11/2001 | Shin et al. | | |
| 2002/0007664 A1 * | 1/2002 | Shin | ............... | A61B 5/02035 73/54.07 |
| 2002/0014111 A1 * | 2/2002 | Shin | ............... | A61B 5/02035 73/54.13 |
| 2002/0148281 A1 * | 10/2002 | Shin | ............... | A61B 5/02035 73/54.01 |
| 2002/0184941 A1 * | 12/2002 | Shin | ............... | A61B 5/02035 73/54.01 |
| 2003/0005752 A1 * | 1/2003 | Shin | ............... | A61B 5/02035 73/54.01 |
| 2003/0066341 A1 * | 4/2003 | Shin | ............... | A61B 5/02035 73/54.07 |
| 2003/0066342 A1 * | 4/2003 | Shin | ............... | A61B 5/02035 73/54.07 |
| 2004/0194538 A1 | 10/2004 | Kensey et al. | | |
| 2004/0253734 A1 | 12/2004 | Firmin | | |
| 2006/0070426 A1 * | 4/2006 | Pelletier | ............... | G01N 11/04 73/54.02 |
| 2009/0158820 A1 * | 6/2009 | Bostrom | ............... | E21B 49/08 73/61.53 |
| 2014/0105446 A1 | 4/2014 | Maxey et al. | | |
| 2015/0122016 A1 * | 5/2015 | Tozzi | ............... | G01N 9/26 73/32 R |

OTHER PUBLICATIONS

Yang et al., Mobile Phone Enabled Pervasive Measurement of Liquid Viscosity, Applied Rheology vol. 21, Issue 6, 2011.

* cited by examiner

YIELD STRESS MEASUREMENT DEVICE AND RELATED METHODS

BACKGROUND

The present application relates to a yield stress measurement device and related methods.

Wellbore operations relating to hydrocarbon exploration and production often use a variety of complex fluids. An important property of a wellbore fluid is its rheology, and specific rheological parameters are intended for specific wellbore operations. For example, in drilling operations, a drilling fluid should be sufficiently viscous to suspend particulate weighting agents and drilled cuttings and to carry the cuttings to the well surface, but not so viscous to be unpumpable or cause formation damage. Formation damage may be caused when the drilling fluid exerts too much pressure on the walls of the wellbore such that cracks form and extend into the surrounding formation. These cracks may then become locations for the drilling fluid to leak from the wellbore into the formation and cause loss circulation issues.

The yield stress of a fluid is one rheological property that relates to the amount of energy needed to initiate flow of the fluid. Currently, yield stress is measured with a rheometer or viscometer, which is a specialized piece of equipment. Operation of some rheometers and viscometers at a well site may be ambiguous and time-consuming. Additionally, the equipment may have several moving parts such that if the equipment breaks in the field, it is often more efficient to replace the equipment than repair on-site, which may delay the wellbore operation.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
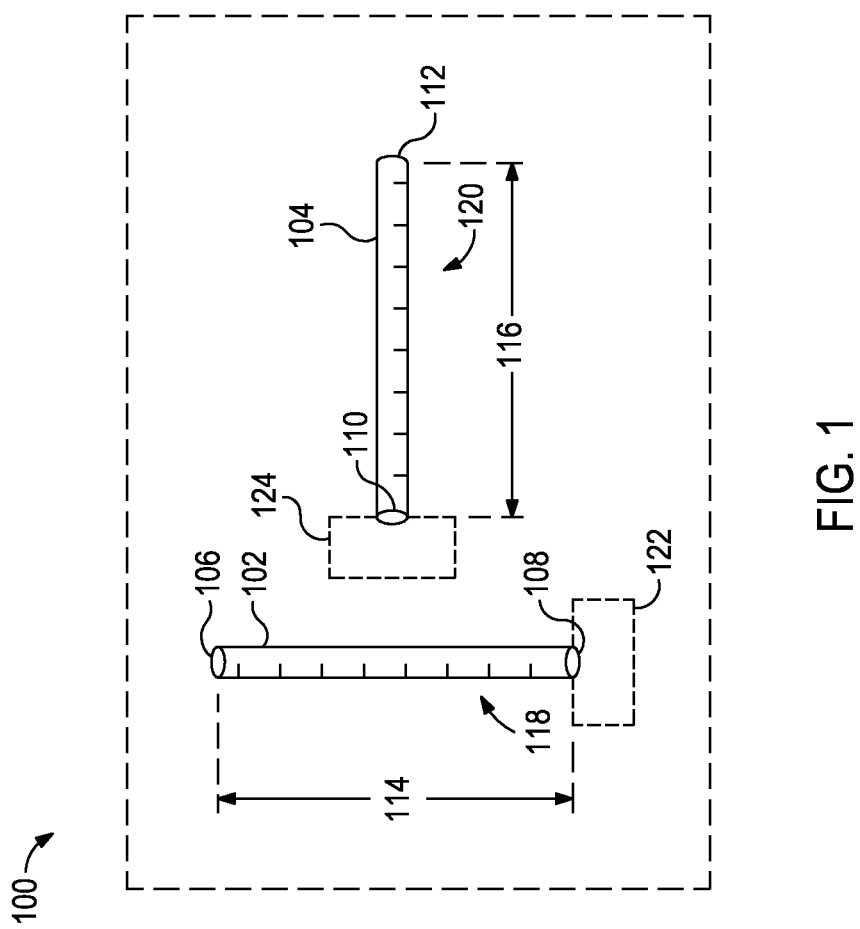
FIG. 1 provides an illustrative diagram of an exemplary yield stress measurement device with a vertical capillary tube and a horizontal capillary tube according to at least some embodiments of the present disclosure.

The present application relates to a yield stress measurement device and related methods. Specifically, the yield stress measurement device and methods use a two-capillary tube setup that measures the amount of a fluid drawn into each capillary and correlates that to the yield stress of the fluid. The devices and methods described herein may be particularly useful for in-the-field measurements because of the simplicity and ease of use.

Generally, the device and methods described herein utilize a horizontal capillary and a vertical capillary tube where the extent to which a fluid is drawn into the capillary tubes may be used to calculate the yield stress of the fluid. Because the devices are uncomplicated, inexpensive, and, in some instances, disposable, they may be well suited for use at a well site.

Without being limited by theory, the yield stress of a fluid is related to the surface tension of the fluid. In the horizontal position, movement of a fluid through the capillary is governed by capillary forces and friction forces on the wall of the capillary, which is mathematically described in Equation 1.

$$\tau_w \pi d_h x = \frac{\pi d_h^2}{4} \Delta P \qquad \text{Equation 1}$$

where: $\tau_w$ is the wall stress, which equals the fluid yield stress in equilibrium $d_h$ is the inner diameter of the horizontal capillary tube x is the distance the fluid flows into the horizontal capillary tube $\Delta P$ is the pressure drop across the horizontal capillary tube Assuming that the contact angle is zero (i.e., perfect wetting of the fluid on the surface of the capillary inner wall), the pressure drop across the horizontal capillary tube is related to the liquid surface tension, which is mathematically described in Equation 2.

$$\Delta P = \frac{4\sigma}{d_h} \qquad \text{Equation 2}$$

where: $\sigma$ is the surface tension of the fluid

Then, combining Equations 1 and 2 and using the steady state conditions (i.e., the maximum distance the fluid flows into the capillary tube) yields Equation 3.

$$\tau_0 = \frac{\sigma}{x_0} \qquad \text{Equation 3}$$

where: $\tau_0$ is the yield stress of the fluid $x_0$ is the maximum distance the fluid flows into the horizontal capillary tube Because it is often not convenient to directly measure the surface tension of the fluid, a vertically positioned capillary can be used to derive the surface tension. In the vertical position, the surface tension is balanced by gravity, which is mathematically described in Equation 4.

$$\frac{4\sigma}{d_v} = \rho g h \qquad \text{Equation 4}$$

where: $\rho$ is the viscosity of the fluid g is the gravitational constant h is the maximum distance the fluid flows into the vertical capillary tube $d_v$ is the inner diameter of the vertical capillary tube Combining Equations 3 and 4 yields Equation 5 for calculating the yield stress of the fluid using a two-capillary tube setup described herein.

$$\tau_0 = \frac{\rho g h d_v}{4 x_0} \qquad \text{Equation 5}$$

Preferably, the horizontal and vertical capillary tubes are the same construction (i.e., have the same inner diameter and are formed of the same material). However, for instances where capillary tubes of are formed of different materials, it is preferred that the materials forming the capillary tubes have comparable contact angles with the fluid (i.e., having contact angles within about 10%). Further, different inner diameters of capillary tubes may be used without amending the equations provided that the inner diameter of both capillary tubes are sized such that the movement of the fluid through both of the capillary tubes is governed by capillary forces and frictional forces. Generally, suitable inner diameters are less than about 2 mm but may depend on the material of construction at the larger inner diameters.

It should be noted that "the maximum distance" a fluid flows into a capillary tube does not necessarily refer to a true maximum but rather a distance that is within about 90% of the maximum.

Measuring the maximum distance a fluid flows into a capillary tube may be achieved by a number of methods. For example, the capillary may have a length scale associated with it (e.g., similar to a graduated cylinder or a ruler separate from, but along the length of, the capillary tube). In another example, the capillary tube may be of a known length and the maximum distance may be derived therefrom (e.g., with optical viewing and analysis software that may be on a computer, cell phone, or other mobile device). In yet another example, the capillary tube may have one or more sensors associated therewith that detects the distance the fluid flows into the capillary tube (e.g., a laser sensor that analyzes light scattering through the capillary tube). One skilled in the art would recognize the capillary tube opacity needed to perform the various methods of measuring the maximum distance the fluid flows into the capillary tube. For example, the mass of the capillary tube may be measured where the distance traveled into the capillary tube is calculated based on the capillary tube dimensions and the density (or specific gravity) of the fluid.

The maximum distance measurement may be taken after an amount of time for the fluid to flow the maximum distance. The amount of time may be a set amount of time (e.g., about 10 seconds to about 30 minutes depending on the fluid). In some instances, the amount of time may be determined by viewing the fluid flowing into the capillary tube, and when a visible change is no longer apparent, the maximum distance may be measured. In some instance, sensors or optical viewing/analysis devices may be configured for a time-lapsed measurement (e.g., time lapsed photography) of the distance the fluid flows into in the capillary tube. Then, the maximum distance may be associated with a threshold rate of change for the fluid distance into the capillary tube. For example, once the fluid flows at less than about 5% increments, the maximum distance may be recorded.

Capillary tubes suitable for use in conjunction with the devices and methods described herein may be formed of materials like glass, polymers (e.g., polyethylene, polypropylene, polyethylene terephthalate, polyvinyl chloride, polystyrene, bioplastics, and the like), and metals. The capillary tubes may have a native (i.e., unfunctionalized and uncoated) interior surface. In some instances, the interior surface of the capillary tube may be coated to provide anti-coagulation with, for example, sodium and ammonium salts.

Capillary tubes suitable for use in conjunction with the devices and methods described herein may have inner diameters up to about 2 mm (e.g., about 10 microns to about 2 mm). When selecting a capillary tube, the inner diameter should be sufficiently large that particulates in the fluid do not clog the capillary tube. For example, some drilling fluids may include particulate weighting agents (e.g., barite and ilmenite) and/or particulate viscosifiers (e.g., bentonite and organically-modified bentonite). The size of such particulates should be considered when selecting a capillary tube diameter.

FIG. 1 provides an illustrative diagram of an exemplary yield stress measurement device 100 with a vertical capillary tube 102 and a horizontal capillary tube 104 according to at least some embodiments of the present disclosure. It should be noted that the terms "horizontal capillary tube," "vertical capillary tube," and the like are used for clarity. Generally, the capillary tubes are substantially perpendicular (i.e., within about 10° of perpendicular) to each other and, during operation the device 100, would be positioned so that the capillary tubes are within about 10° of either vertical or horizontal.

Each of the vertical and horizontal capillary tubes 102, 104 have two open ends 106,108 and 110,112, respectively, and a length 114,116, respectively, extending therebetween. Coupled to the lengths 114,116 of the vertical and horizontal capillary tubes 102,104 are a first and second length scale 118,120, respectively (illustrated as graduations on the vertical and horizontal capillary tubes 102,104). In the presently illustrated device 100, the extent to which a fluid flows into the vertical and horizontal capillary tubes 102,104 may be measured by eye or other suitable detector (e.g., a camera coupled to suitable analysis software) given the graduations on the vertical and horizontal capillary tubes 102,104.

The device 100 further includes a first fluid area 122 for maintaining a fluid in contact with the bottom end 108 of the vertical capillary tube 102 and a second fluid area 124 for maintaining a fluid in contact with one end 110 of the horizontal capillary tube 104. Because of the horizontal angle of the horizontal capillary tube 104, the second fluid area 124 may be associated with either end of the horizontal capillary tube 104.

The fluid areas 122,124 should be configured to maintain the fluid in contact with the appropriate end 108,110 of the capillary tube 102,104, respectively. Exemplary fluid areas may be a depression, a well, a reservoir, or the like suitable for containing fluid and maintaining the necessary fluid-to-end contact. Another example of a fluid area configuration may be a surface that provides for a contact angle relative to the fluid sufficient for a drop(s) of the fluid on the surface to maintain the necessary fluid-to-end contact.

Figure 2:
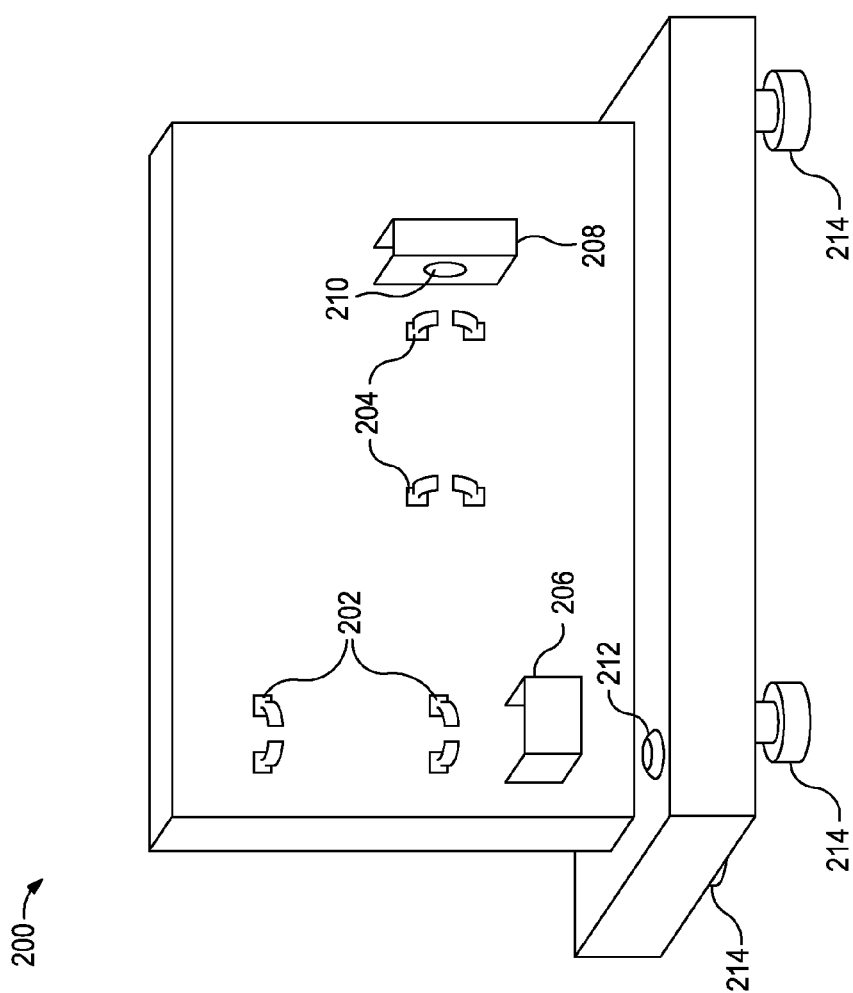
FIG. 2 provides an illustrative diagram of an exemplary yield stress measurement device according to at least some embodiments of the present disclosure.

FIG. 2 provides an illustrative diagram of an exemplary yield stress measurement device 200 according to at least some embodiments of the present disclosure. The device 200 includes a vertical capillary tube holder 202 with a corresponding fluid area, illustrated as a reservoir 206, for maintaining the fluid-to-end contact between the bottom of a capillary tube in the vertical capillary tube holder 202 and a fluid contained in the reservoir 206. The device 200 also includes a horizontal capillary tube holder 204 with a corresponding fluid area, illustrated as a reservoir 208. The reservoir 208 has a port 210 where the horizontal capillary can adjoin with the reservoir 208 for maintaining the fluid-to-end contact between one end of a capillary tube in the horizontal capillary tube holder 204 and a fluid contained in the reservoir 208. Additionally, the device includes a leveling sensor 212 (e.g., a bubble level) and height-adjustable feet 214 for leveling the device 200, which may be useful in the field to more accurately position the capillary tubes horizontal and vertical.

While FIG. 2 illustrates the capillary tube holders 202,204 as brackets, other holder configurations may be used. For example, depressions in the device may be used as positional guides and a spring-loaded strut may be used to hold the capillary tubes in place. In another example, clamps may be used as an alternative to brackets. In yet another example, magnets may be used in conjunction with metal capillary tubes that are magnetic or capillary tubes with a magnetic portion.

Figure 3:
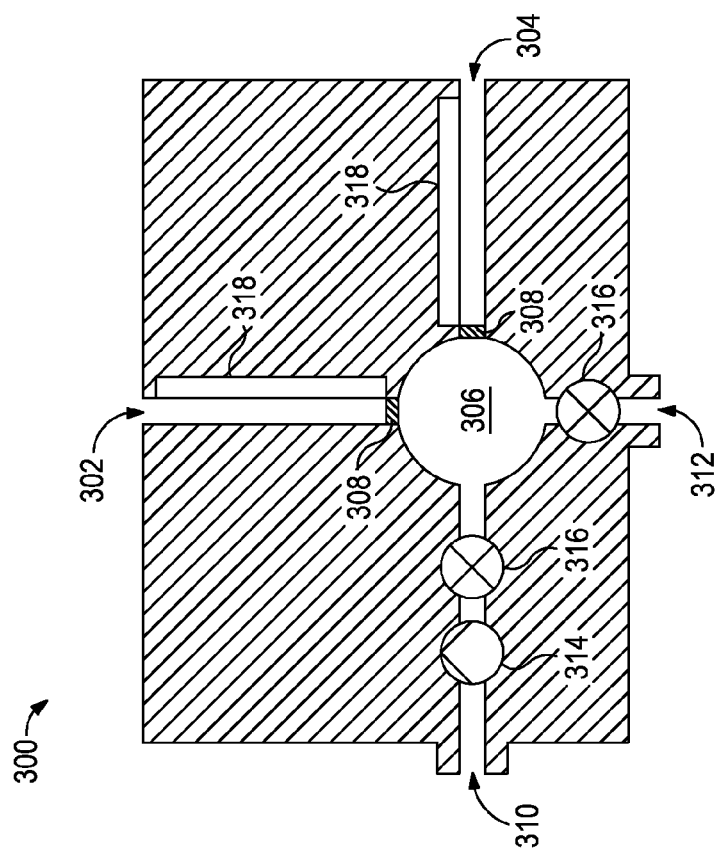
FIG. 3 provides an illustrative cross-sectional diagram of an exemplary yield stress measurement device according to at least some embodiments of the present disclosure.

FIG. 3 provides an illustrative cross-sectional diagram of an exemplary yield stress measurement device 300 according to at least some embodiments of the present disclosure. The device 300 may be automated with a vertical slot 302 and a horizontal slot 304 configured for receiving the capillary tubes. The slots 302,304 may extend to a reservoir 306. Further, each slot 302,304 may have a seal 308 (or alternatively a valve) that allows for sealing the reservoir 306 when capillary tubes are not in the slots 302,304. The reservoir 306 may have extending therefrom a fluid inlet port 310 and a fluid outlet port 312 for loading the fluid into the reservoir 306, removing the fluid from the reservoir 306, and cleaning the reservoir 306. As illustrated, the fluid inlet port 310 has a pump 314 coupled thereto for transporting the fluid of interest or the cleaning fluids, and both fluid inlet and outlet ports 310,312 have a valve 316 for sealing the reservoir 306. When allowing the fluid to traverse the capillary tubes in one or more of the slots 302,304, one or both of the inlet and outlet ports 310,312 should be open to balance the atmospheric pressure.

Coupled to the slots 302,304 are detectors 318 for measuring the maximum distance the fluid flows into the capillary tubes in the slots 302,304. The detectors 318 may produce output signals corresponding to the maximum distances, which may then be transmitted to a display coupled thereto or to a signal processor coupled thereto for calculating the yield stress based on the maximum distances. In some instances, the device 300 may be configured to provide the maximum distances measured by the detectors 318 or the calculated yield stress as a readout on the device 300. Alternatively, the device 300 may be configured to be connected to an electronic device (e.g., a computer, cell phone, or electronic tablet) with a signal processor that is configured to receive the output signals corresponding to the maximum distances measured by the detectors 318, calculate the yield stress, and display the yield stress (or alternatively provide the yield stress to a program that monitors, calculates, and/or controls the parameters of the wellbore operations).

The methods and devices of the present disclosure may be useful for measuring the yield stress of a wellbore fluid. Exemplary wellbore fluids may include, but are not limited to, drilling fluids, acidizing fluids, fracturing fluids, completion fluids, and the like.

Wellbore fluids may be composed of a base fluid and various additives dissolve, suspend, or otherwise dispersed therein. Examples of base fluids may include, but not be limited to, oil-based fluids, aqueous-based fluids, aqueous-miscible fluids, water-in-oil emulsions, or oil-in-water emulsions. Examples of additives may include salts, weighting agents, inert solids, fluid loss control agents, emulsifiers, dispersion aids, corrosion inhibitors, emulsion thinners, emulsion thickeners, viscosifying agents (e.g., polymers, clays, hydrophobically-modified clays, and the like), gelling agents, surfactants, proppant particulates, gravel particulates, lost circulation materials, foaming agents, gases, pH control additives, breakers, biocides, crosslinkers, stabilizers, chelating agents, scale inhibitors, gas hydrate inhibitors, mutual solvents, oxidizers, reducers, friction reducers, clay stabilizing agents, filtration control agents, rheology modifiers, and the like, and any combination thereof.

In some embodiments, the yield stress of a wellbore fluid (e.g., a drilling fluid) may be measured with a yield stress measurement device described herein. Based on that measurement, the composition of the wellbore fluid may be altered to change the yield stress of the wellbore fluid (e.g., by changing the concentration of a viscosifier, a weighting agent, or a fluid loss control agent therein). Then, the altered wellbore fluid may be used in a wellbore operation (e.g., drilling a wellbore penetrating a subterranean formation).

In some embodiments, during a wellbore operation, the yield stress of a wellbore fluid (e.g., a drilling fluid) circulating through the wellbore may be measured with a yield stress measurement device described herein. If needed, the composition of the wellbore fluid may be altered to change the yield stress of the wellbore fluid. This may be particularly useful in drilling operations where removing the cuttings from the drilling fluid may remove other components of the drilling fluid that should be replenished to provide the proper drilling fluid yield stress for the parameters of the drilling operations.

In some embodiments, the yield stress of a wellbore fluid may be measured during or before a wellbore operations with a yield stress measurement device described herein. Then, the parameter of the wellbore operation may be changed in response to the measured yield stress of the wellbore fluid. For example, in a drilling operation, the flow rate, penetration rate into the formation, fluid composition (e.g., the oil/water ratio, concentration of individual components, and the like), pipe rotation, mud weight, wellbore pressure (also referred to as equivalent circulation density), temperature, and the like may be altered to account for changes in the yield stress of the drilling fluid.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Embodiments disclosed herein include Embodiment A, Embodiment B, and Embodiment C.

Embodiment A is a method that includes maintaining a first capillary tube having two open ends and an inner cavity in a horizontal position; contacting one of the two open ends of a first capillary tube with a fluid, the fluid being present in an amount sufficient to maintain at least some of the fluid outside the first capillary tube as the fluid flows into the inner cavity of the first capillary tube; measuring a first maximum distance the fluid flows into the inner cavity of first capillary tube; maintaining a second capillary tube having two open ends and an inner cavity in a vertical position; contacting a bottom end of the second capillary tube with the fluid, the fluid being present in an amount sufficient to maintain at least some of the fluid outside the second capillary tube as the fluid flows into the inner cavity of the second capillary tube; measuring a second maximum distance the fluid flows into the inner cavity of the second capillary tube; and calculating a yield stress of the fluid based on the first maximum distance and the second maximum distance.

Embodiment A may have one or more of the following additional elements in any combination: Element A1: wherein measuring the first maximum distance involves taking an image or series of images of the fluid in the first capillary tube and analyzing the image or series of images; Element A2: Embodiment A1 wherein analyzing the image or series of images is automated; Element A3: wherein the fluid is a drilling fluid and the method further comprises: drilling a wellbore penetrating a subterranean formation with the drilling fluid; Element A4: wherein the fluid is a drilling fluid and the method further comprises: drilling a wellbore penetrating a subterranean formation with the drilling fluid; and changing an operational parameter of the drilling based on the yield stress of the drilling fluid; Element A5: wherein the fluid is a first drilling fluid and the method further comprises: changing a composition of the first drilling fluid to yield a second drilling fluid and drilling a wellbore penetrating a subterranean formation with the second drilling fluid; Element A6: wherein the fluid is a wellbore fluid and the method further comprises: performing a wellbore operation with the wellbore fluid; Element A7: wherein the fluid is a wellbore fluid and the method further comprises: performing a wellbore operation with the wellbore fluid; and adjusting a parameter of the wellbore operation based on the yield stress of the wellbore fluid; and Element A8: wherein measuring the first maximum distance and measuring the second maximum distance are performed by at least one detector that produces a first output signal and a second output signal corresponding to the first maximum distance and the second maximum distance, respectively, wherein the method further involves transmitting the first and second output signals to a signal processor, and wherein calculating the yield stress is performed by the signal processor.

By way of non-limiting example, exemplary combinations applicable to Embodiment A include: combinations of Element A1 in combination with Element A8 and optionally Element A2; the foregoing in combination with at least one of Elements A3-A7; Element A4 in combination with Element A5; Element A1 and optionally Element A2 in combination with at least one of Elements A3-A7; and Element A8 in combination with at least one of Elements A3-A7.

Embodiment B is a yield stress measurement apparatus that includes a first capillary tube and a second capillary tube substantially perpendicular to each other, each capillary tube having two open ends and a length extending therebetween; a first and second length scale corresponding to the lengths of the first and second capillary tubes, respectively; and a first fluid area and a second fluid area at one of the open ends of each of the first and second capillary tubes, respectively.

Embodiment C is a yield stress measurement apparatus that includes a first capillary tube holder and a second capillary tube holder substantially perpendicular to each other; a first and second length scale corresponding to a length of the first and second capillary tube holders, respectively; and a first and second fluid area positioned relative to the first and second capillary tube holders, respectively, to allow for fluid contact between a fluid disposed therein and an open end of a first and second capillary disposed in the first and second capillary tube holders, respectively.

Embodiments B and C may have one or more of the following additional elements in any combination: Element B1: the apparatus further including at least one detector configured to measure and produce an output signal corresponding to distances a fluid flows into the first and second capillary tubes; Element B2: the apparatus further including Element B1 and a display coupled to the at least one detector and configured to receive the output signals and display the distances; Element B3: the apparatus further including Element B1 and a signal processor coupled to the at least one detector and configured to receive the output signals, calculate a yield stress of the fluid, and produce a second output signal corresponding to the yield stress of the fluid; Element B4: the apparatus further including Element B3 and a display coupled to the at least one detector and configured to receive the second output signal and display the yield stress; Element B5: the apparatus further including Element B1 and a signal processor coupled to the at least one detector and configured to receive the output signals, calculate a yield stress of the fluid, and calculate at least one parameter of a wellbore operation based on the yield stress of the fluid; Element B6: wherein the first and second fluid areas are the same; and Element B7: element B6 wherein the first and second fluid areas are a reservoir and the apparatus further comprises: a pump configured to transport a fluid into the reservoir.

By way of non-limiting example, exemplary combinations applicable to Embodiment B include: Element B2 in combination with Element B3 and optionally Element B4 where the displays may be the same display or different displays; Element B5 in combination with the foregoing; Element B2 in combination with Element B5; Element B5 in combination with Element B3 and optionally Element B4; Element B6 and optionally Element B7 in combination with any of the foregoing; Element B1 in combination with Element B6 and optionally Element B7; Element B2 in combination with Element B6 and optionally Element B7; Element B5 in combination with Element B6 and optionally Element B7; and Element B3 and optionally Element B4 in combination with Element B6 and optionally Element B7.

To facilitate a better understanding of the embodiments of the present invention, the following examples of preferred or representative embodiments are given. In no way should the following examples be read to limit, or to define, the scope of the invention.

EXAMPLES

The yield stress of a water-based mud (or drilling fluid) and an oil-based mud were measured with a two-capillary method described herein and a rheometer. The water-based mud with a density of about 12.9 pounds per gallon (ppg) included water as the base fluid, a viscosifier, and barite as a weighting agent. The oil-based mud with a density of about 13.2 ppg included ENCORE® base (100% isomerized olefin-based fluid, available from Halliburton Energy Services, Inc.) as the base fluid, an emulsifier, and barite as weighting agent.

Figure 4:
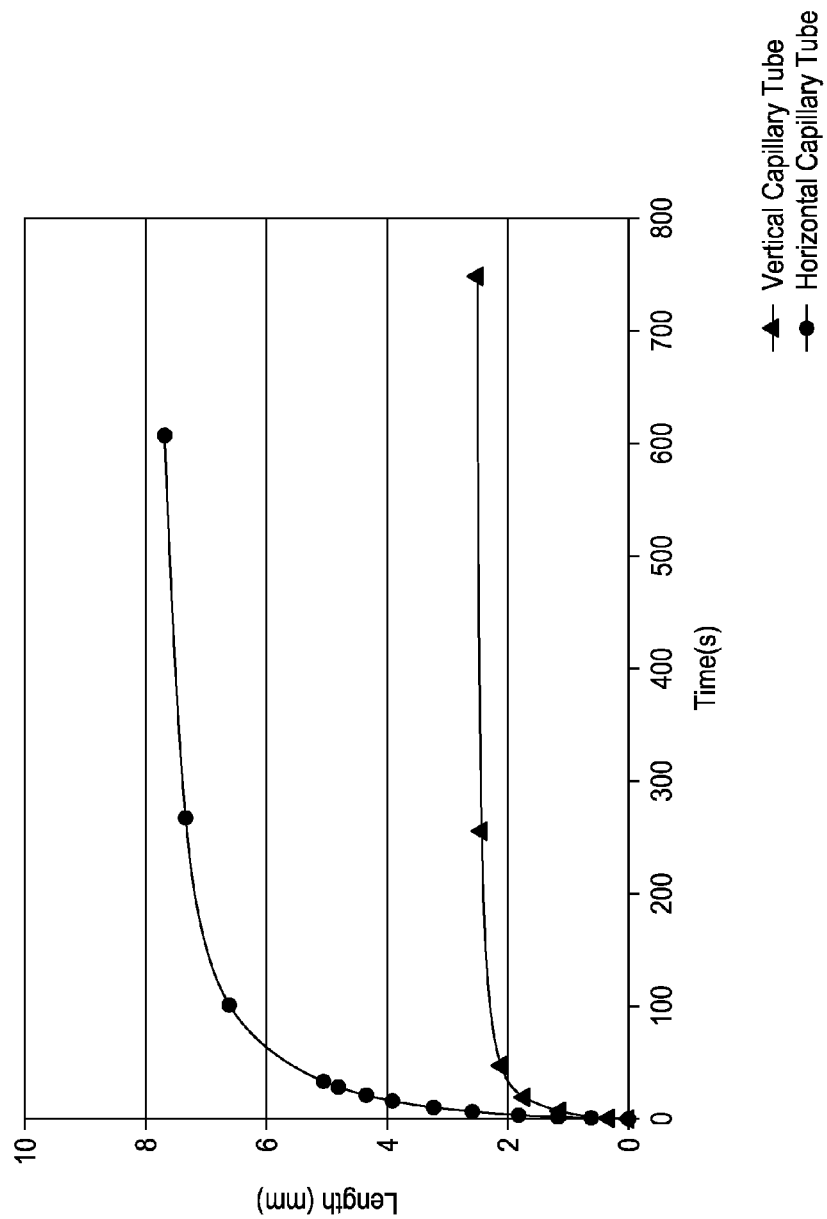
FIG. 4 provides a plot of the distance a water-based mud flowed into horizontal and vertical capillaries as a function of time.
Figure 5:
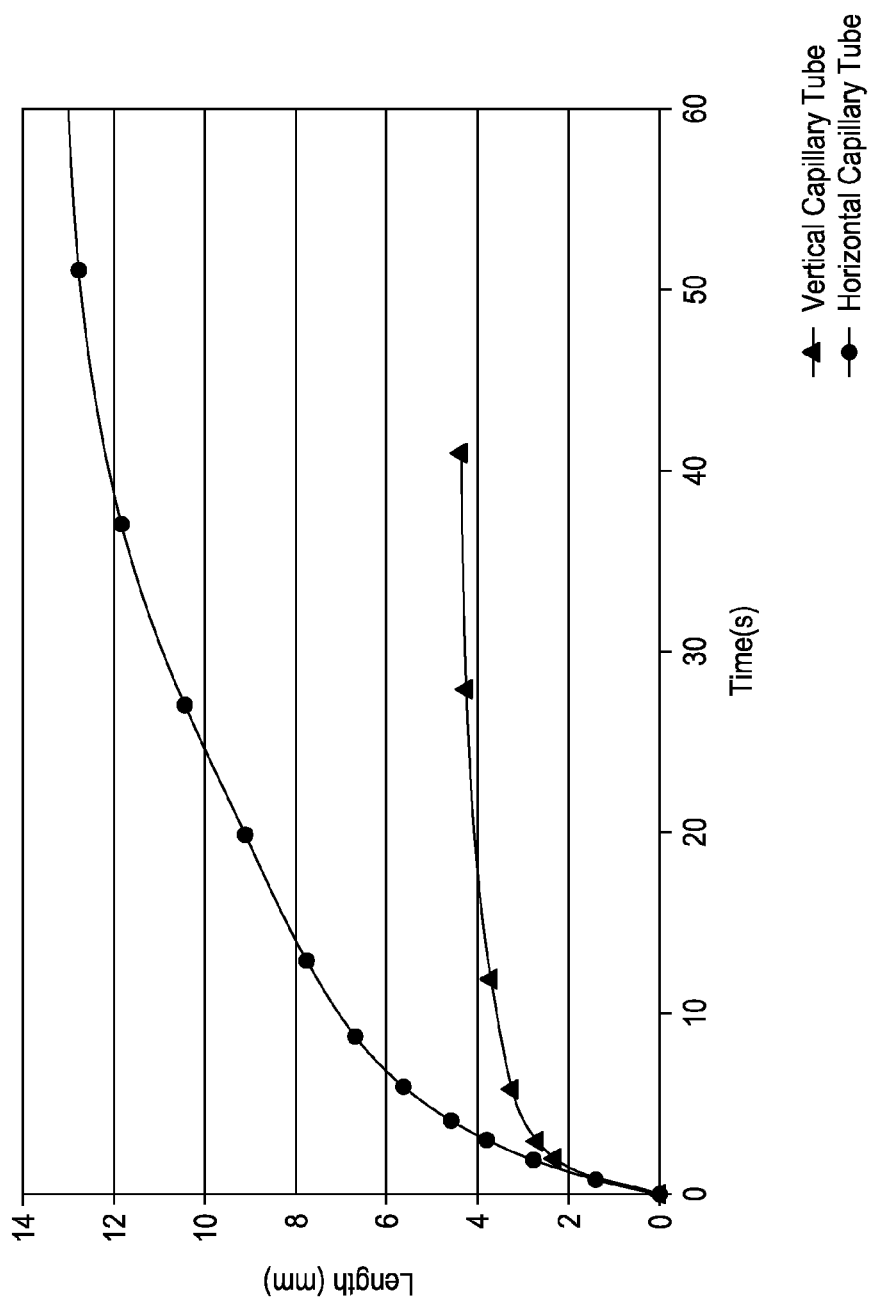
FIG. 5 provides a plot of the distance an oil-based mud flowed into horizontal and vertical capillaries as a function of time.

When allowing the fluids to draw into the vertical and horizontal capillary tubes (glass capillary tubes with a 1.08 mm inner diameter), time-lapsed photography was used to monitor the distance the fluid flowed into the capillary tubes. FIGS. 4 and 5 provides the distances for the water-based mud and oil-based mud, respectively. The water-based mud reached a maximum distance in the vertical capillary tube of about 2.25 mm in about 60 seconds and in the horizontal capillary tube of about 7.5 mm in about 4.5 minutes. The oil-based mud reached a maximum distance in the vertical capillary tube of about 4.25 mm in about 30 seconds and in the horizontal capillary tube of about 13 mm in about 50 seconds. The calculated yield stress from the capillary measurements was about 1.6 Pa for the water-based mud and about 1.3 Pa for the oil-based mud. When measured with a rheometer, the yield stress for the water-based mud was about 1.66 Pa and for the oil-based mud was about 1.3 Pa. The calculated values from the two-capillary method and the measured values from the rheometer are in good agreement and illustrate efficacy of the methods and devices described herein.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   maintaining a first capillary tube having two open ends and an inner cavity in a horizontal position;
   contacting one of the two open ends of a first capillary tube with a fluid, the fluid being present in an amount sufficient to maintain at least some of the fluid outside the first capillary tube as the fluid flows into the inner cavity of the first capillary tube;
   measuring a first maximum distance the fluid flows into the inner cavity of first capillary tube;
   maintaining a second capillary tube having two open ends and an inner cavity in a vertical position;
   contacting a bottom end of the second capillary tube with the fluid, the fluid being present in an amount sufficient to maintain at least some of the fluid outside the second capillary tube as the fluid flows into the inner cavity of the second capillary tube;
   measuring a second maximum distance the fluid flows into the inner cavity of the second capillary tube; and
   calculating a yield stress of the fluid based on the first maximum distance and the second maximum distance.

2. The method of claim 1, wherein the fluid is a drilling fluid and the method further comprises: drilling a wellbore penetrating a subterranean formation with the drilling fluid.

3. The method of claim 1, wherein the fluid is a drilling fluid and the method further comprises: drilling a wellbore penetrating a subterranean formation with the drilling fluid; and changing an operational parameter of the drilling based on the yield stress of the drilling fluid.

4. The method of claim 1, wherein the fluid is a first drilling fluid and the method further comprises: changing a composition of the first drilling fluid to yield a second drilling fluid and drilling a wellbore penetrating a subterranean formation with the second drilling fluid.

5. The method of claim 1, wherein the fluid is a wellbore fluid and the method further comprises: performing a wellbore operation with the wellbore fluid.

6. The method of claim 1, wherein the fluid is a wellbore fluid and the method further comprises: performing a wellbore operation with the wellbore fluid; and adjusting a parameter of the wellbore operation based on the yield stress of the wellbore fluid.

7. The method of claim 1, wherein measuring the first maximum distance and measuring the second maximum distance are performed by at least one detector that produces a first output signal and a second output signal corresponding to the first maximum distance and the second maximum distance, respectively, wherein the method further involves transmitting the first and second output signals to a signal processor, and wherein calculating the yield stress is performed by the signal processor.

8. The method of claim 1, wherein measuring the first maximum distance involves taking an image or series of images of the fluid in the first capillary tube and analyzing the image or series of images.

9. The method of claim 3, wherein analyzing the image or series of images is automated.

10. A yield stress measurement apparatus comprising:
    a first capillary tube and a second capillary tube substantially perpendicular to each other, each capillary tube having two open ends and a length extending therebetween;
    a first and second length scale corresponding to the lengths of the first and second capillary tubes, respectively; and a first fluid area and a second fluid area at one of the open ends of each of the first and second capillary tubes, respectively.

11. The apparatus of claim 10 further comprising:
at least one detector configured to measure and produce an output signal corresponding to distances a fluid flows into the first and second capillary tubes.

12. The apparatus of claim 11 further comprising:
a display coupled to the at least one detector and configured to receive the output signals and display the distances.

13. The apparatus of claim 11 further comprising:
a signal processor coupled to the at least one detector and configured to receive the output signals, calculate a yield stress of the fluid, and calculate at least one parameter of a wellbore operation based on the yield stress of the fluid.

14. The apparatus of claim 11 further comprising:
a signal processor coupled to the at least one detector and configured to receive the output signals, calculate a yield stress of the fluid, and produce a second output signal corresponding to the yield stress of the fluid.

15. The apparatus of claim 14 further comprising:
a display coupled to the at least one detector and configured to receive the second output signal and display the yield stress.

16. The apparatus of claim 10, wherein the first and second fluid areas are the same.

17. The apparatus of claim 16, wherein the first and second fluid areas are a reservoir and the apparatus further comprises: a pump configured to transport a fluid into the reservoir.

18. A yield stress measurement apparatus comprising:
a first capillary tube holder and a second capillary tube holder substantially perpendicular to each other;
a first and second length scale corresponding to a length of the first and second capillary tube holders, respectively; and
a first and second fluid area positioned relative to the first and second capillary tube holders, respectively, to allow for fluid contact between a fluid disposed therein and an open end of a first and second capillary disposed in the first and second capillary tube holders, respectively.

19. The apparatus of claim 18 further comprising:
at least one detector positioned relative to the first and second capillary tube holders to measure distances the fluid flows into the first capillary tube and a second capillary tube.

* * * * *